United States Patent [19]

Kosuge et al.

[11] 4,381,935
[45] May 3, 1983

[54] OXIMECARBAMATE DERIVATIVES, AND THEIR PRODUCTION AND USE

[75] Inventors: Yoshiaki Kosuge, Hyogo; Ryo Yoshida, Kawanishi; Seizo Sumida; Hirofumi Oshita, both of Hyogo; Soji Otsuki, Sonehigashimachi; Katsuzo Kamoshita, Osaka, all of Japan

[73] Assignee: Sumitomo Chemical Company, Limited, Osaka, Japan

[21] Appl. No.: 317,889

[22] Filed: Nov. 3, 1981

Related U.S. Application Data

[62] Division of Ser. No. 65,838, Aug. 13, 1979, Pat. No. 4,315,768.

[30] Foreign Application Priority Data

Aug. 25, 1978 [JP] Japan .................. 53-104127

[51] Int. Cl.³ ............... A01N 43/08; A01N 47/20; C07C 131/105; C07C 317/48
[52] U.S. Cl. ........................... 71/88; 71/79; 71/98; 71/115; 71/116; 260/453.8; 549/438; 549/441
[58] Field of Search ............ 260/453.8; 71/88, 98, 71/111, 121, 115–116, 79; 549/438, 441

[56] References Cited

U.S. PATENT DOCUMENTS 3,576,834  4/1971  Buchanan ............... 260/453.8

*Primary Examiner*—Glennon H. Hollrah
*Assistant Examiner*—L. Hendriksen
*Attorney, Agent, or Firm*—Birch, Stewart, Kolasch & Birch

[57] ABSTRACT

Oximecarbamate derivatives of the formula:

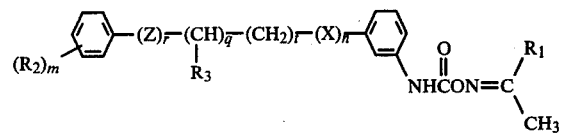

wherein $R_1$ is methyl or methoxy, $R_2$ is lower alkyl, lower alkoxy, methylenedioxy, methylthio, halogen or trifluoromethyl, $R_3$ is hydrogen, methyl or ethyl, X and Z are each oxygen or sulfur, m is an integer of 0 to 5 when $R_2$ is fluorine or an integer of 0 to 3 when $R_2$ is other than fluorine, $R_2$ being same or different in case of m being an integer of 2 or 3, n and r are each an integer of 0 or 1 but when one of them is zero, the other is not zero, q is an integer of 0 or 1 and t is an integer of 0 to 4, which are useful as herbicides having high selectivity to crop plants.

10 Claims, No Drawings

OXIMECARBAMATE DERIVATIVES, AND THEIR PRODUCTION AND USE

This application is a divisional of copending application Ser. No. 065,838, filed on Aug. 13, 1979, now U.S. Pat. No. 4,315,768.

The present invention relates to oximecarbamate derivatives, and their production and use. More particularly, it relates to oximecarbamate derivatives of the formula:

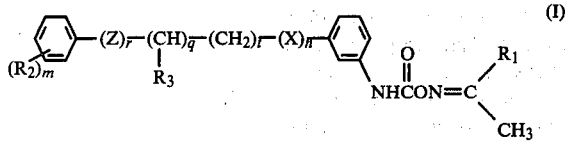

wherein $R_1$ is methyl or methoxy, $R_2$ is lower alkyl, lower alkoxy, methylenedioxy, methylthio, halogen or trifluoromethyl, $R_3$ is hydrogen, methyl or ethyl, X and Z are each oxygen or sulfur, m is an integer of 0 to 5 when $R_2$ is fluorine only or an integer of 0 to 3 when any $R_2$ is other than fluorine, $R_2$ being same or different in case of m being an integer of 2 or 3, n and r are each an integer of 0 or 1 but when one of them is zero, the other is not zero, q is an integer of 0 or 1 and t is an integer of 0 to 4, and their preparation processes and their use as herbicides.

In the above significance, the term "lower" indicates usually the ones having not more than 5 carbon atoms. Examples of lower alkyl are methyl, ethyl, n-propyl, isopropyl, t-butyl, etc. Examples of lower alkoxy are methoxy, ethoxy, n-propoxy, isopropoxy, t-butoxy, etc. Examples of halogen are fluorine, chlorine, bromine, etc.

The purpose of the present invention is to provide herbicides useful for controlling and exterminating weeds without any unfavorable influence on the growth of crop Needless to say, a herbicide is desirable to have high safety to crop plants. However, a herbicide for post-emergence application attaches not only onto the foliage of weeds but also onto the foliage of crop plants so that the extermination of only the weeds is hardly possible. In fact, commercially available herbicides of this type are quite few.

It has now been found that the oximecarbamate derivatives (I) of the present invention can control and exterminate efficiently weeds without causing any chemical injury to crop plants such as soybean, cotton, sugar beet and wheat by post-emergence application. For instance, the compounds (I) can exterminate redroot pigweed (*Amaranthus retroflexus*), sunflower (*Helianthus annuus*), cocklebur (*Xanthium pennsylvanicum*), annual morningglory (*Ipomoea pupurea*), crabgrass (*Digitaria adscendens*), barnyard grass (*Echinochloa crus-galli*), etc. in the field of cotton or soybean, and common lambsquarter (*Chenopodium album*), radish, black nightshade (*Solanum nigrum*), green foxtail (*Setaria viridis*), etc. in the field of sugar beet or wheat with high safety to the crop plants, when applied after emergence of the weeds. Thus, they are useful as selective herbicides for post-emergence treatment in the field of cotton, soybean, sugar beet or wheat.

Further, the compounds (I) show a herbicidal activity by soil treatment of paddy fields. For instance, their application to rice paddy fields can exterminate barnyard grass (*Echinochloa crus-galli*), pickerel weed (*Monochoria vaginalis*), false pimpernel (*Lindernia pyxidaria*), toothcup (*Rotala indica*), nutsedge sp. (*Cyperus difformis*), etc. without causing any chemical injury onto rice plants.

While the oximecarbamate derivatives (I) are novel, there is known O-(N-phenylcarbamoyl)acetoxime (W. German Pat. No. 1,024,746; Control (a)). However, any herbicidal activity of this control (a) compound on foliage treatment is never known. In fact, its herbicidal activity on foliage treatment is much inferior to that of the compounds (I).

The excellent herbicidal activity of the compounds (I) may be attributed to their characteristic features in chemical structure. Namely, they are characteristic in having a substituent such as substituted phenoxy, substituted phenylthio, substituted phenylalkyloxy, substituted phenylalkylthio, substituted phenoxyalkyl, substituted phenylthioalkyl, substituted phenoxyalkyloxy or phenylthioalkyloxy at the m-position of the phenyl group in the O-(N-phenylcarbamoyl)oxime derivative. For instance, as hereinafter shown, the herbicidal activity of O-[N-{4-(2-fluorophenoxymethyl)phenyl}carbamoyl]acetoxime (Control (b)) or of O-[N-{4-(3-(4-chlorophenyl)propoxy)phenyl}carbamoyl]acetoxime (Control (c)) is much inferior to the herbicidal activity of the compounds (I).

In general, the compounds (I) exhibit a high selectivity to soybean, cotton, sugar beet and wheat. The selectivity is extremely associated with the structure. For instance, O-[N-{3-(3-chlorophenoxymethyl)phenyl}-carbamoyl]acetoxime (Compound No. 21) shows selectivity to cotton and sugar beet. When the chlorine atom at the m-position is changed to a trifluoromethyl group, the resulting compound (Compound No. 32) shows selectivity to soybean and wheat losing selectivity to sugar beet and cotton. Further, when the methyl group in the dimethylacetoxime group of Compound No. 32 is replaced by a methoxy group, the resultant compound (Compound No. 33) shows selectivity to sugar beet and wheat losing selectivity to soybean. Furthermore, O-[N-{3-(3-chlorophenethyloxy)phenyl}carbamoyl]methoxyethanaloxime (Compound No. 103) shows selectivity only to wheat.

The compounds (I) are novel and can be produced, for instance, by reacting a phenylisocyanate derivative of the formula:

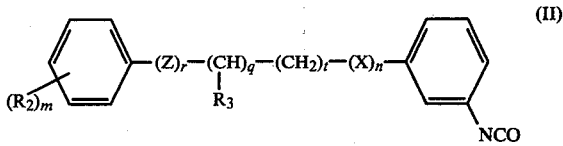

wherein $R_2$, $R_3$, X, Z, m, n, r, q and t are each as defined above, with an oxime derivative of the formula:

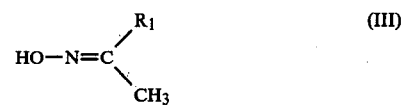

wherein $R_1$ is as defined above.

The reaction may be carried out in an inert organic solvent (e.g. benzene, toluene, xylene, diethyl ether, tetrahydrofuran, dioxane, N,N-dimethylformamide, chloroform, carbon tetrachloride). The presence of a tertiary amine (e.g. pyridine, triethylamine, diethylaniline) in the reaction system is advantageous for effecting the reaction efficiently. Usually, the oxime derivative (III) is employed in an equimolar to excessive molar amount, preferably in an equimolar to 1.5 fold amount, to the phenylisocyanate derivative (II).

The reaction is effected usually at a temperature from 0° to 100° C. and sometimes under cooling or heating, and it is normally completed within about 10 hours. The reaction product can be recovered from the reaction mixture by a conventional separation procedure such as filtration or distillation. If necessary, the recovered product may be further purified, for instance, by recrystallization or column chromatography.

Still, the phenylisocyanate derivative (II) and the oxime derivative (III) are known.

Practical and presently preferred embodiments of the preparation of the compounds (I) are illustratively shown in the following examples.

EXAMPLE 1

To a solution of acetoxime (8.1 g) in benzene (100 ml), there was dropwise added a solution of m-(3,4-dichlorophenoxymethyl)phenylisocyanate (29.4 g) in benzene (50 ml) at 10° to 20° C. The mixture was stirred at the same temperature for 3 hours, and thereafter the solvent was removed. The residue was recrystallized from a mixture of benzene and tetrahydrofuran (5:1 by volume) to obtain 25.3 g of white needles (Compound No. 36). M.P., 79°–81° C.

Elementary analysis: Calcd. for $C_{17}H_{16}Cl_2N_2O_3$: C, 55.59%; H, 4.40%; N, 7.63%; Cl, 19.30%. Found: C, 55.56%; H, 4.25%; N, 7.70%; Cl, 19.44%.

EXAMPLE 2

To a solution of methoxyethanaloxime (8.9 g) in toluene (150 ml), there was added triethylamine (0.2 g). To this solution, there was dropwise added a solution of m-(4-tert-butylphenoxymethyl)phenylisocyanate (28.1 g) in toluene (60 ml) at 50°–60° C. The mixture was stirred at the same temperature for 2 hours, and thereafter the solvent was removed. The oily substance obtained was purified by column chromatography (silica gel, 70–230 mesh) using a mixture of benzene and tetrahydrofuran (8:1 by volume) to obtain 16.7 g of an oily substance (Compound No. 27). $n_D^{25}$: 1.5590.

Elementary analysis: Calcd. for $C_{21}H_{26}N_2O_4$: C, 68.07; H, 7.09; N, 7.56%. Found: C, 68.13; H, 7.12%; N, 7.44%.

Some specific examples of the compound (I), which can be prepared in the same manner as above, are shown in Table 1 below but the compounds of the invention are not limited to these examples.

TABLE 1

| Compound No. | Chemical structure | Melting point or refractive index |
| --- | --- | --- |
| 1 | (phenyl)-O-(phenyl)-NHCON=C(CH₃)(CH₃) | M.P., 119–120° C. |
| 2 | Cl-(phenyl)-S-(phenyl)-NHCON=C(CH₃)(CH₃) | M.P., 77–79° C. |
| 3 | (Cl-phenyl)-O-(phenyl)-NHCON=C(CH₃)(CH₃) | M.P., 71–75° C. |
| 4 | (F₃C-phenyl)-O-(phenyl)-NHCON=C(CH₃)(CH₃) | $n_D^{23}$ 1.5445 |
| 5 | (F₃C-phenyl)-O-(phenyl)-NHCON=C(OCH₃)(CH₃) | $n_D^{23}$ 1.5312 |

TABLE 1-continued

| Compound No. | Chemical structure | Melting point or refractive index |
|---|---|---|
| 6 | 3,4-Cl$_2$-C$_6$H$_3$-O-C$_6$H$_4$-NHCON=C(CH$_3$)$_2$ | $n_D^{25.5}$ 1.5918 |
| 7 | 3-CH$_3$-4-Cl-C$_6$H$_3$-O-C$_6$H$_4$-NHCON=C(CH$_3$)$_2$ | $n_D^{25.5}$ 1.5882 |
| 8 | 4-F$_3$C-C$_6$H$_4$-O-C$_6$H$_4$-NHCON=C(OCH$_3$)(CH$_3$) | M.P., 58–60° C. |
| 9 | 3,4-(CH$_3$)$_2$-C$_6$H$_3$-O-C$_6$H$_4$-NHCON=C(CH$_3$)$_2$ | M.P., 119–121° C. |
| 10 | 3,5-Cl$_2$-C$_6$H$_3$-O-C$_6$H$_4$-NHCON=C(CH$_3$)$_2$ | M.P., 107–108° C. |
| 11 | 3-H$_3$CO-C$_6$H$_4$-O-C$_6$H$_4$-NHCON=C(CH$_3$)$_2$ | M.P., 59–60° C. |
| 12 | 2,4-(CH$_3$)$_2$-C$_6$H$_3$-O-C$_6$H$_4$-NHCON=C(OCH$_3$)(CH$_3$) | $n_D^{22}$ 1.5735 |
| 13 | 2,4-(CH$_3$)$_2$-C$_6$H$_3$-O-C$_6$H$_4$-NHCON=C(CH$_3$)$_2$ | M.P., 95.5–96.5 |
| 14 | 3-F$_3$C-C$_6$H$_4$-O-C$_6$H$_4$-NHCON=C(CH$_3$)$_2$ | M.P., 80–82° C. |

TABLE 1-continued

| Compound No. | Chemical structure | Melting point or refractive index |
|---|---|---|
| 15 | phenyl-OCH₂-phenyl-NHCON=C(OCH₃)(CH₃) | $n_D^{24}$ 1.5671 |
| 16 | phenyl-OCH₂-phenyl-NHCON=C(CH₃)(CH₃) | M.P., 47.5–49.5° C. |
| 17 | Cl-phenyl-SCH₂-phenyl-NHCON=C(CH₃)(CH₃) | M.P., 89–91° C. |
| 18 | 2-F-phenyl-OCH₂-phenyl-NHCON=C(CH₃)(CH₃) | M.P., 97–98° C. |
| 19 | 3-F-phenyl-OCH₂-phenyl-NHCON=C(CH₃)(CH₃) | M.P., 10–13° C. |
| 20 | 3-F-phenyl-OCH₂-phenyl-NHCON=C(CH₃)(OCH₃) | $n_D^{26}$ 1.5691 |
| 21 | 3-Cl-phenyl-OCH₂-phenyl-NHCON=C(CH₃)(CH₃) | M.P., 59–61° C. |
| 22 | 3-Br-phenyl-OCH₂-phenyl-NHCON=C(CH₃)(CH₃) | M.P., 76–77° C. |
| 23 | 2-CH₃-phenyl-OCH₂-phenyl-NHCON=C(CH₃)(CH₃) | M.P., 76–77° C. |

TABLE 1-continued

| Compound No. | Chemical structure | Melting point or refractive index |
|---|---|---|
| 24 | H₃C—⟨⟩—OCH₂—⟨⟩—NHCON=C(CH₃)₂ | $n_D^{24}$ 1.5821 |
| 25 | (i)H₇C₃—⟨⟩—OCH₂—⟨⟩—NHCON=C(CH₃)₂ | $n_D^{22.5}$ 1.5478 |
| 26 | (t)H₉C₄—⟨⟩—OCH₂—⟨⟩—NHCON=C(CH₃)₂ | M.P., 98–100° C. |
| 27 | (t)H₉C₄—⟨⟩—OCH₂—⟨⟩—NHCON=C(OCH₃)(CH₃) | $n_D^{25}$ 1.5590 |
| 28 | H₃CO—⟨⟩—OCH₂—⟨⟩—NHCON=C(CH₃)₂ | $n_D^{24}$ 1.5771 |
| 29 | H₃CO—⟨⟩—OCH₂—⟨⟩—NHCON=C(CH₃)₂ | $n_D^{21}$ 1.5800 |
| 30 | H₅C₂O—⟨⟩—OCH₂—⟨⟩—NHCON=C(CH₃)₂ | $n_D^{23}$ 1.5645 |
| 31 | H₃CS—⟨⟩—OCH₂—⟨⟩—NHCON=C(CH₃)₂ | M.P., 81–82° C. |
| 32 | F₃C—⟨⟩—OCH₂—⟨⟩—NHCON=C(CH₃)₂ | $n_D^{27}$ 1.5496 |

TABLE 1-continued

| Compound No. | Chemical structure | Melting point or refractive index |
|---|---|---|
| 33 | 3-CF$_3$-C$_6$H$_4$-OCH$_2$-C$_6$H$_4$-NHCON=C(OCH$_3$)(CH$_3$) | $n_D^{24}$ 1.5852 |
| 34 | 4-C$_2$H$_5$-C$_6$H$_4$-OCH$_2$-C$_6$H$_4$-NHCON=C(CH$_3$)$_2$ | $n_D^{24}$ 1.5793 |
| 35 | 3-CF$_3$-C$_6$H$_4$-OCH(CH$_3$)-C$_6$H$_4$-NHCON=C(CH$_3$)$_2$ | $n_D^{25.5}$ 1.5341 |
| 36 | 3,4-Cl$_2$-C$_6$H$_3$-OCH$_2$-C$_6$H$_4$-NHCON=C(CH$_3$)$_2$ | M.P., 79–81° C. |
| 37 | 3,5-Cl$_2$-C$_6$H$_3$-OCH$_2$-C$_6$H$_4$-NHCON=C(CH$_3$)$_2$ | M.P., 36–37° C. |
| 38 | 3,5-Cl$_2$-C$_6$H$_3$-OCH$_2$-C$_6$H$_4$-NHCON=C(OCH$_3$)(CH$_3$) | $n_D^{25}$ 1.5778 |
| 39 | 3,5-Cl$_2$-C$_6$H$_3$-OCH(CH$_3$)-C$_6$H$_4$-NHCON=C(CH$_3$)$_2$ | $n_D^{27.5}$ 1.5750 |
| 40 | 3-CH$_3$-4-Cl-C$_6$H$_3$-OCH$_2$-C$_6$H$_4$-NHCON=C(CH$_3$)$_2$ | M.P., 89–90° C. |
| 41 | 3-CF$_3$-4-Cl-C$_6$H$_3$-OCH$_2$-C$_6$H$_4$-NHCON=C(CH$_3$)$_2$ | M.P., 83–85° C. |

TABLE 1-continued

| Compound No. | Chemical structure | Melting point or refractive index |
| --- | --- | --- |
| 42 | 3,4-(methylenedioxy)phenyl-O-CH₂-C₆H₄-NHCON=C(CH₃)₂ | M.P., 84–86° C. |
| 43 | 3,4-(methylenedioxy)phenyl-O-CH₂-C₆H₄-NHCON=C(OCH₃)(CH₃) | M.P., 45–50° C. |
| 44 | 3,5-(F₃C)₂C₆H₃-OCH₂-C₆H₄-NHCON=C(CH₃)₂ | $n_D^{25.5}$ 1.5739 |
| 45 | 3,4,5-Cl₃C₆H₂-OCH₂-C₆H₄-NHCON=C(CH₃)₂ | $n_D^{25}$ 1.5891 |
| 46 | 3,5-Cl₂-4-CH₃O-C₆H₂-OCH₂-C₆H₄-NHCON=C(CH₃)₂ | M.P., 83–84° C. |
| 47 | 4-Cl-3,5-(CH₃)₂-C₆H₂-OCH₂-C₆H₄-NHCON=C(CH₃)₂ | M.P., 115–117° C. |
| 48 | 2,6-Cl₂-4-CH₃-C₆H₂-OCH₂-C₆H₄-NHCON=C(CH₃)₂ | M.P., 110–112° C. |
| 49 | C₆F₅-OCH₂-C₆H₄-NHCON=C(CH₃)₂ | $n_D^{25.5}$ 1.5305 |
| 50 | C₆H₅-CH₂O-C₆H₄-NHCON=C(CH₃)₂ | M.P., 116–117° C. |

TABLE 1-continued

| Compound No. | Chemical structure | Melting point or refractive index |
|---|---|---|
| 51 | 3-Cl-C6H4-CH2O-C6H4-NHCON=C(CH3)2 | M.P., 77–78° C. |
| 52 | 3-Cl-C6H4-CH2O-C6H4-NHCON=C(CH3)(OCH3) | M.P., 79.5–81° C. |
| 53 | 4-Cl-C6H4-CH2O-C6H4-NHCON=C(CH3)2 | M.P., 128–129° C. |
| 54 | 2-CH3-C6H4-CH2O-C6H4-NHCON=C(CH3)2 | M.P., 120–122° C. |
| 55 | 4-H3C-C6H4-CH2O-C6H4-NHCON=C(CH3)2 | M.P., 108–110° C. |
| 56 | 4-(t)H9C4-C6H4-CH2O-C6H4-NHCON=C(CH3)2 | M.P., 126–127° C. |
| 57 | 3,4-Cl2-C6H3-CH2O-C6H4-NHCON=C(CH3)2 | $n_D^{22.5}$ 1.5919 |
| 58 | 4-F-C6H4-(CH2)2S-C6H4-NHCON=C(CH3)2 | $n_D^{24}$ 1.5975 |
| 59 | 4-Cl-C6H4-(CH2)2O-C6H4-NHCON=C(CH3)2 | $n_D^{27}$ 1.5770 |
| 60 | 4-Cl-C6H4-(CH2)2O-C6H4-NHCON=C(CH3)(OCH3) | M.P., 99–100° C. |

TABLE 1-continued

| Compound No. | Chemical structure | Melting point or refractive index |
|---|---|---|
| 61 | 2-CH₃-C₆H₄-(CH₂)₂O-C₆H₄-NHCON=C(CH₃)₂ | M.P., 95–96° C. |
| 62 | (i)H₉C₄-C₆H₄-(CH₂)₂S-C₆H₄-NHCON=C(CH₃)₂ | $n_D^{27}$ 1.5845 |
| 63 | 3-H₃CO-C₆H₄-(CH₂)₂O-C₆H₄-NHCON=C(CH₃)₂ | $n_D^{27}$ 1.5689 |
| 64 | 3-H₃CO-C₆H₄-(CH₂)₂O-C₆H₄-NHCON=C(OCH₃)(CH₃) | M.P., 78–82° C. |
| 65 | 3-H₃CO-C₆H₄-(CH₂)₂S-C₆H₄-NHCON=C(CH₃)₂ | $n_D^{23.5}$ 1.5970 |
| 66 | 4-H₃C-C₆H₄-CH(CH₃)CH₂O-C₆H₄-NHCON=C(CH₃)₂ | $n_D^{27.5}$ 1.5587 |
| 67 | C₆H₅-(CH₂)₃O-C₆H₄-NHCON=C(CH₃)₂ | $n_D^{26.5}$ 1.5593 |
| 68 | 3,4-Cl₂-C₆H₃-(CH₂)₃O-C₆H₄-NHCON=C(CH₃)₂ | $n_D^{30}$ 1.5861 |
| 69 | 3,4-Cl₂-C₆H₃-(CH₂)₃O-C₆H₄-NHCON=C(OCH₃)(CH₃) | $n_D^{30}$ 1.5762 |

TABLE 1-continued

| Compound No. | Chemical structure | Melting point or refractive index |
|---|---|---|
| 70 | 3-Cl-C6H4-O(CH2)2O-C6H4-NHCON=C(CH3)2 | M.P., 87–89° C. |
| 71 | 2,4-Cl2-C6H3-O(CH2)2O-C6H4-NHCON=C(CH3)2 | M.P., 89.5–91° C. |
| 72 | 2,4-Cl2-C6H3-OCH2CH2O-C6H4-NHCON=C(OCH3)(CH3) | M.P., 54–56° C. |
| 73 | 4-H3C-C6H4-O(CH2)2O-C6H4-NHCON=C(CH3)2 | M.P., 89.5–91° C. |
| 74 | 4-H3C-C6H4-S(CH2)2O-C6H4-NHCON=C(CH3)2 | M.P., 64–66° C. |
| 75 | 3-F3C-C6H4-O(CH2)2O-C6H4-NHCON=C(CH3)2 | M.P., 106.5–107.5° C. |
| 76 | 4-Cl-C6H4-S(CH2)2O-C6H4-NHCON=C(CH3)2 | M.P., 55–57° C. |
| 77 | C6F5-O(CH2)2O-C6H4-NHCON=C(CH3)2 | $n_D^{28}$ 1.5233 |
| 78 | C6H5-(CH2)5O-C6H4-NHCON=C(CH3)2 | $n_D^{26}$ 1.5590 |
| 79 | 4-H3C-C6H4-O(CH2)3O-C6H4-NHCON=C(CH3)2 | M.P., 163–166° C. |

TABLE 1-continued

| Compound No. | Chemical structure | Melting point or refractive index |
|---|---|---|
| 80 | C₆H₅-CH(C₂H₅)CH₂CH₂O-C₆H₄-NHCON=C(CH₃)₂ | M.P., 84–86.5° C. |
| 81 | C₆H₅-CH(CH₃)CH₂CH₂O-C₆H₄-NHCON=C(CH₃)₂ | $n_D^{24.5}$ 1.5608 |
| 82 | 3-CH₃-C₆H₄-CH₂O-C₆H₄-NHCON=C(CH₃)₂ | $n_D^{24.5}$ 1.5786 |
| 83 | 2,4-(CH₃)₂-C₆H₃-(CH₂)₃O-C₆H₄-NHCON=C(CH₃)₂ | $n_D^{25.5}$ 1.5675 |
| 84 | 4-Cl-C₆H₄-(CH₂)₃O-C₆H₄-NHCON=C(CH₃)₂ | $n_D^{24.5}$ 1.5770 |
| 85 | 2-F-C₆H₄-(CH₂)₃O-C₆H₄-NHCON=C(CH₃)₂ | $n_D^{24.5}$ 1.5556 |
| 86 | 4-(CH₃)₃C-C₆H₄-CH₂CH₂O-C₆H₄-NHCON=C(CH₃)₂ | M.P., 98–99.5° C. |
| 87 | 4-(CH₃)₃C-C₆H₄-CH₂CH₂O-C₆H₄-NHCON=C(CH₃)(OCH₃) | $n_D^{30}$ 1.5515 |
| 88 | 4-H₃CO-C₆H₄-CH₂CH₂CH₂O-C₆H₄-NHCON=C(CH₃)₂ | M.P., 58–60° C. |

TABLE 1-continued

| Compound No. | Chemical structure | Melting point or refractive index |
|---|---|---|
| 89 | H₃CO-C₆H₄-CH₂CH₂O-C₆H₄-NHCON=C(CH₃)₂ | $n_D^{29.5}$ 1.5666 |
| 90 | 2-CH₃O-C₆H₄-CH₂CH₂CH₂O-C₆H₄-NHCON=C(CH₃)₂ | $n_D^{27}$ 1.5516 |
| 91 | 3-H₃C-C₆H₄-CH₂CH₂CH₂O-C₆H₄-NHCON=C(CH₃)₂ | $n_D^{28}$ 1.5742 |
| 92 | 3-Cl-C₆H₄-CH₂CH₂CH₂O-C₆H₄-NHCON=C(OCH₃)(CH₃) | $n_D^{27}$ 1.5632 |
| 93 | 4-H₃C-C₆H₄-CH₂CH₂CH₂CH₂O-C₆H₄-NHCON=C(CH₃)₂ | $n_D^{29.5}$ 1.5649 |
| 94 | 2-CH₃-C₆H₄-SCH₂CH₂O-C₆H₄-NHCON=C(CH₃)₂ | M.P., 53–55° C. |
| 95 | 2-CH₃-C₆H₄-CH(CH₃)CH₂O-C₆H₄-NHCON=C(CH₃)₂ | $n_D^{21}$ 1.5569 |
| 96 | 2-CH₃-C₆H₄-CH(CH₃)CH₂CH₂O-C₆H₄-NHCON=C(OCH₃)(CH₃) | $n_D^{21}$ 1.5618 |
| 97 | 4-H₃C-C₆H₄-CH₂CH₂O-C₆H₄-NHCON=C(CH₃)₂ | $n_D^{29.5}$ 1.5599 |

TABLE 1-continued

| Compound No. | Chemical structure | Melting point or refractive index |
|---|---|---|
| 98 | H₃C—⟨C₆H₄⟩—CH₂CH₂O—⟨C₆H₄⟩—NHCON=C(CH₃)(OCH₃) | M.P., 61–64° C. |
| 99 | 2-CH₃-⟨C₆H₄⟩—CH₂CH₂O—⟨C₆H₄⟩—NHCON=C(CH₃)(OCH₃) | M.P., 68–70° C. |
| 100 | 2-Cl-⟨C₆H₄⟩—CH₂CH₂O—⟨C₆H₄⟩—NHCON=C(CH₃)(CH₃) | M.P., 89–90° C. |
| 101 | 2-Cl-⟨C₆H₄⟩—CH₂CH₂O—⟨C₆H₄⟩—NHCON=C(OCH₃)(CH₃) | $n_D^{24.5}$ 1.5739 |
| 102 | 3-Cl-⟨C₆H₄⟩—CH₂CH₂O—⟨C₆H₄⟩—NHCON=C(CH₃)(CH₃) | $n_D^{27}$ 1.5648 |
| 103 | 3-Cl-⟨C₆H₄⟩—CH₂CH₂O—⟨C₆H₄⟩—NHCON=C(OCH₃)(CH₃) | M.P., 71–72.5° C. |
| 104 | 2-CH₃-⟨C₆H₄⟩—CH₂CH₂CH₂O—⟨C₆H₄⟩—NHCON=C(CH₃)(CH₃) | $n_D^{29.5}$ 1.5592 |
| 105 | 2-CH₃-⟨C₆H₄⟩—CH₂CH₂CH₂O—⟨C₆H₄⟩—NHCON=C(OCH₃)(CH₃) | $n_D^{21}$ 1.5708 |
| 106 | ⟨C₆H₅⟩—(CH₂)₅S—⟨C₆H₄⟩—NHCON=C(CH₃)(CH₃) | $n_D^{29}$ 1.5950 |

TABLE 1-continued

| Compound No. | Chemical structure | Melting point or refractive index |
|---|---|---|
| 107 | Cl—⟨C6H4⟩—CH2CH2CH2CH2O—⟨C6H4⟩—NHC(O)N=C(CH3)(CH3) | M.P., 65-66° C. |
| 108 | 2-CH3, 4-H3C—⟨C6H3⟩—CH2CH2O—⟨C6H4⟩—NHC(O)N=C(CH3)(OCH3) | $n_D^{26.5}$ 1.5605 |
| 109 | 2-CH3—⟨C6H4⟩—OCH2CH2O—⟨C6H4⟩—NHC(O)N=C(CH3)(CH3) | M.P., 102-104° C. |
| 110 | 2-CH3—⟨C6H4⟩—OCH2CH2O—⟨C6H4⟩—NHC(O)N=C(OCH3)(CH3) | M.P., 81-83° C. |

In the practical use of the compounds (I), they may be applied as such or in any preparation form such as wettable powders, emulsifiable concentrates, granules, fine granules or dusts.

In producing such preparation form, a solid or liquid carrier may be used. As for the solid carrier, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be given alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphates, fatty acid salts, alkyl sulfates, alkyl sulfonates, alkylaryl sulfonates, alkyl phosphates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the compound (I) may be from 1 to 95% by weight, preferably from 1 to 80% by weight.

Practical embodiments of the herbicidal composition according to the invention are illustratively shown in the following examples wherein parts and % are by weight.

PREPARATION EXAMPLE 1

Eighty parts of Compound No. 36, 5 parts of polyoxyethylene alkylaryl ether and 15 parts of synthetic silicon oxide hydrate are well mixed while being powdered to obtain a wettable powder.

PREPARATION EXAMPLE 2

Thirty parts of Compound No. 21, 7 parts of polyoxyethylene alkylaryl ether, 3 parts of alkylaryl sulfonate and 60 parts of xylene are well mixed to obtain an emulsifiable concentrate.

PREPARATION EXAMPLE 3

One part of Compound No. 69, 1 part of white carbon, 5 parts of ligninsulfonate and 93 parts of clay are well mixed while being powdered. The mixture is then well kneaded with water, granulated and dried to obtain a granule.

PREPARATION EXAMPLE 4

Fourty parts of bentonite, 5 parts of ligninsulfonate and 55 parts of clay are well mixed while being powdered. The mixture is then well kneaded with water, granulated and dried to obtain a granule containing no active ingredient. The granule is then impregnated with 5 parts of Compound No. 32 to obtain a granule.

PREPARATION EXAMPLE 5

Three parts of Compound No. 27, 0.5 part of isopropyl phosphate, 66.5 parts of clay and 30 parts of talc are well mixed while being powdered to obtain a dust.

The compounds (I) of the invention may be used together with other herbicides to improve their activity as herbicides, and in some cases, a synergistic effect can be expected. As the other herbicides, there may be given phenoxy series herbicides such as 2,4-dichlorophenoxyacetic acid, 2-methyl-4-chlorophenoxyacetic acid and 2,4-dichlorophenoxybutyric acid (including esters and salts thereof); diphenyl ether series herbicides such as 2,4-dichlorophenyl-4'-nitrophenyl ether, 2,4,6-trichlorophenyl-4'-nitrophenyl ether, 2,4-dichloro-3'-methoxy-4'-nitrophenyl ether, 2,4-dichlorophenyl-3'-methoxycarbonyl-4'-nitrophenyl ether and 2-chloro-4-trifluoromethylphenyl-3'-hydroxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazine, 4-amino-3-methyl-6-phenyl-1,2,4-triazine-5(4H)-one and 4-amino-6-tert-butyl-3-methylthio-1,2,4-triazine-5(4H)-one; urea series herbicides such as 3-(3,4-dichlorophenyl)-1,1-dimethylurea, 3-(3,4-dichlorophenyl)-1-methoxy-1-methylurea, 3-(3-chloro-4-difluorochloromethylthiophenyl)-1,1-dimethylurea, 3-[4-(4-chlorophenoxy)phenyl]-1,1-dimethylurea and 3-($\alpha,\alpha,\alpha$-trifluoro-m-tolyl)-1,1-dimethylurea; carbamate series herbicides such as isopropyl-N-(3-chlorophenyl)carbamate, methyl-N-(3,4-dichlorophenyl)carbamate and 4-chloro-2-butynyl-m-chlorocarbanilate; thiolcarbamate series herbicides such as S-(4-chlorobenzyl)-N,N-diethylthiolcarbamate, S-ethyl-N,N-hexamethylenethiolcarbamate and S-ethyl dipropylthiolcarbamate; acid anilide series herbicides such as 3,4-dichloropropionanilide, N-methoxymethyl-2,6-diethyl-2-chloroacetanilide and 2-chloro-2',6'-diethyl-N-(butoxymethyl)acetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N-(phosphonomethyl)glycine, O-methyl-O-(2-nitro-5-methylphenyl)-N-sec-butylphosphoroamidothioate and O-ethyl-O-(2-nitro-4-methylphenyl)-N-isopropylphosphoroamidothioate; toluidine series herbicides such as $\alpha,\alpha,\alpha$-trifluoro-2,6-dinitro-N,N-dipropyl-p-toluidine, N-(cyclopropylmethyl)-$\alpha,\alpha,\alpha$-trifluoro-2,6-dinitro-N-propyl-p-toluidine; N-sec-butyl-4-tert-butyl-2,6-dinitroaniline; 3,5-dinitro-4-N,N-dipropylaminosulfanylamide; 5-tert-butyl-3-(2,4-dichloro-5-isopropoxyphenyl)-1,3,4-oxadiazolin-2-one; 3-isopropyl-1H-2,1,3-benzothiadiazine(4)-3H-one-2,2-dioxide (including salts thereof); α-(β-naphthoxy)propionanilide; 2-(α-naphthoxy)-N,N-diethylpropionamide; 3-amino-2,5-dichlorobenzoic acid; 2-sec-butyl-4,6-dinitrophenol; N-1-naphthylphthalamic acid; 5-amino-4-chloro-2-phenyl-3(2H)-pyridazine and the like. But, the herbicides are not of course limited to these examples.

The herbicides of the invention may be applied together with fungicides, pyrethroid series insecticides, other insecticides, plant growth regulators, fertilizers, etc.

The dosage rate of the compounds (I) depends upon their kinds, the sorts of cultivated plants, the method of application, etc. Generally, however, the dosage rate is from 2 to 200 grams, preferably from 5 to 50 grams, of the active ingredient per are.

The application of the compounds (I) as herbicides will be illustrated in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of plant.

| Rating value | Fresh weight (percentage to untreated plot) | |
| --- | --- | --- |
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Control (a)

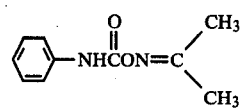

(M.P, 143–145° C.)

Control (b)

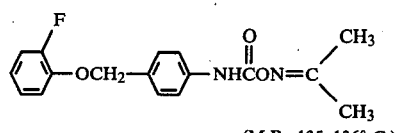

(M.P., 135–136° C.)

Control (c)

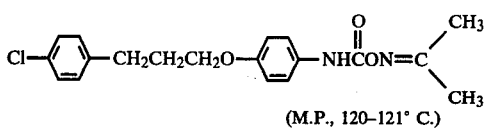

(M.P., 120–121° C.)

MCP

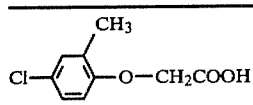

Bentazon

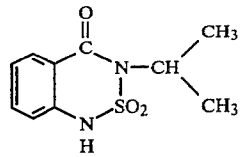

Fluometuron

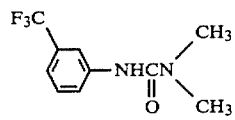

Swep

EXAMPLE I (PADDY RACE TEST)

Wagner's pots (1/5000 are) were each filled with 1.5 kg of paddy field soil containing the seeds of weeds and kept under flooded conditions. The seedlings of rice plant at a 3-leaf stage were transplanted thereto, and after the seeds of barnyard grass were sown therein, the seedlings were grown for 15 days in a green-house. Thereafter, the required amount of the wettable powder of each test compound was diluted with water and applied to the soil under flooded conditions. Twenty-five days after the application, the evaluation of herbicidal activity and phytotoxicity was made on the rice plants and barnyard grass as well as broad-leaved weeds (e.g. pickerel weed (*Monochoria vaginalis*), false pimpernel (*Lindernia pyxidaria*), toothcup (*Rotala indica*)) and nutsedge sp. (*Cyperus difformis*). The results are shown in Table 2.

TABLE 2

| Compound No. | Dosage (weight of active ingredient, g/are) | Rice plant | Barnyard grass | Broad-leaved weed | Nutsedge sp. |
|---|---|---|---|---|---|
| 1 | 20 | 0 | 4 | 4 | 5 |
| 2 | 20 | 0 | 4 | 5 | 5 |
| 3 | 20 | 0 | 5 | 5 | 5 |
|   | 10 | 0 | 4 | 5 | 4 |
| 4 | 20 | 0 | 4 | 5 | 5 |
| 5 | 20 | 0 | 4 | 4 | 4 |
| 6 | 20 | 0 | — | 5 | 4 |
| 7 | 20 | 0 | 4 | 5 | 5 |
| 8 | 20 | 0 | — | 5 | 5 |
| 9 | 20 | 0 | — | 5 | 4 |
| 10 | 20 | 0 | 4 | 5 | 5 |
| 11 | 20 | 0 | — | 5 | 5 |
| 12 | 20 | 0 | 4 | 5 | 5 |
| 13 | 20 | 0 | — | 5 | 5 |
| 14 | 20 | 0 | 5 | 5 | 5 |
| 15 | 20 | 0 | — | 5 | 5 |
| 16 | 20 | 0 | 4 | 5 | 5 |
| 17 | 20 | 0 | 5 | 5 | 4 |
| 18 | 20 | 0 | 5 | 5 | 5 |
| 19 | 10 | 0 | 4 | 5 | 5 |
|   | 20 | 0 | 5 | 5 | 5 |
| 20 | 10 | 0 | 5 | 5 | 5 |
|   | 20 | 0 | 5 | 5 | 5 |
| 21 | 10 | 0 | 5 | 5 | 5 |
|   | 20 | 0 | 5 | 5 | 5 |
| 22 | 10 | 0 | 4 | 5 | 5 |
|   | 20 | 0 | 5 | 5 | 5 |
|   | 10 | 0 | 4 | 5 | 5 |
| 23 | 20 | 0 | — | 5 | 5 |
| 24 | 20 | 0 | 4 | 4 | 5 |
| 25 | 20 | 1 | 5 | 5 | 5 |
| 26 | 20 | 0 | 5 | 5 | 5 |
|   | 10 | 0 | 4 | 5 | 5 |
| 27 | 20 | 0 | 5 | 5 | 5 |
| 28 | 20 | 0 | 4 | 5 | 4 |
| 29 | 20 | 0 | 4 | 5 | 5 |
| 30 | 20 | 0 | — | 5 | 5 |
| 31 | 20 | 0 | — | 4 | 4 |
| 32 | 20 | 0 | 5 | 5 | 5 |
|   | 10 | 0 | 5 | 5 | 5 |
| 33 | 20 | 0 | 4 | 5 | 5 |
| 35 | 20 | 0 | 5 | 5 | 5 |
|   | 10 | 0 | 4 | 5 | 5 |
| 36 | 20 | 0 | 5 | 5 | 5 |
|   | 10 | 0 | 4 | 5 | 5 |
| 37 | 20 | 0 | 5 | 5 | 5 |
|   | 10 | 0 | 5 | 5 | 5 |
| 38 | 20 | 0 | 5 | 5 | 5 |
|   | 10 | 0 | 4 | 5 | 5 |
| 39 | 20 | 0 | 4 | 5 | 4 |
| 40 | 20 | 0 | 4 | 5 | 5 |
|   | 10 | 0 | — | 5 | 4 |
| 41 | 20 | 0 | 5 | 5 | 5 |
|   | 10 | 0 | 4 | 5 | 5 |
| 42 | 20 | 0 | — | 5 | 4 |
| 43 | 20 | 0 | — | 4 | 4 |
| 44 | 20 | 0 | 5 | 5 | 5 |
| 45 | 20 | 0 | 5 | 5 | 5 |
|   | 10 | 0 | 4 | 5 | 5 |
| 46 | 20 | 0 | 4 | 5 | 5 |
| 47 | 20 | 0 | — | 5 | 5 |
| 48 | 20 | 0 | 4 | 5 | 4 |
| 49 | 20 | 0 | 5 | 5 | 5 |
| 50 | 20 | 0 | 5 | 5 | 5 |
| 51 | 20 | 0 | 5 | 5 | 5 |
|   | 10 | 0 | 4 | 5 | 5 |
| 52 | 20 | 0 | 5 | 5 | 5 |
| 53 | 20 | 0 | 4 | 5 | 5 |
| 54 | 20 | 0 | 4 | 5 | 5 |
| 55 | 20 | 0 | 5 | 5 | 5 |
| 56 | 20 | 0 | 5 | 5 | 5 |
|   | 10 | 0 | 4 | 5 | 5 |
| 57 | 20 | 0 | 5 | 5 | 5 |
|   | 10 | 0 | 5 | 5 | 5 |
| 58 | 20 | 0 | — | 5 | 4 |
| 59 | 20 | 0 | 5 | 5 | 5 |
|   | 10 | 0 | 4 | 5 | 5 |
| 60 | 20 | 0 | 5 | 5 | 5 |
| 61 | 20 | 0 | — | 5 | 5 |
| 62 | 20 | 0 | — | 5 | 5 |
| 63 | 20 | 0 | 4 | 4 | 4 |
| 64 | 20 | 0 | 4 | 5 | 5 |
| 65 | 20 | 0 | 4 | 5 | 5 |
| 66 | 20 | 0 | 5 | 5 | 5 |
| 67 | 20 | 0 | — | 4 | 5 |
| 68 | 20 | 0 | — | 5 | 5 |
| 69 | 20 | 0 | 4 | 5 | 5 |
| 70 | 20 | 0 | 4 | 5 | 4 |
| 71 | 20 | 0 | 4 | 5 | 5 |
| 72 | 20 | 0 | — | 5 | 4 |
| 73 | 20 | 0 | — | 5 | 5 |
| 74 | 20 | 0 | 4 | 4 | 4 |
| 75 | 20 | 0 | 4 | 5 | 4 |
| 76 | 20 | 0 | — | 4 | 4 |
| 77 | 20 | 0 | 4 | 5 | 5 |

TABLE 2-continued

| Compound No. | Dosage (weight of active ingredient, g/are) | Rice plant | Barn-yard grass | Broad-leaved weed | Nutsedge sp. |
| --- | --- | --- | --- | --- | --- |
| 78 | 20 | 0 | — | 5 | 4 |
| 79 | 20 | 0 | — | 4 | 4 |
| 80 | 20 | 0 | — | 5 | 5 |
| 81 | 20 | 0 | 4 | 5 | 5 |
| 82 | 20 | 0 | 4 | 5 | 4 |
| 83 | 20 | 0 | 4 | 5 | 5 |
| 84 | 20 | 0 | 5 | 5 | 5 |
|  | 10 | 0 | 4 | 5 | 5 |
| 85 | 20 | 1 | 5 | 5 | 5 |
|  | 10 | 0 | 5 | 5 | 5 |
| 86 | 20 | 0 | 4 | 5 | 4 |
| 87 | 20 | 0 | 4 | 5 | 5 |
| 88 | 20 | 0 | — | 5 | 4 |
| 89 | 20 | 0 | — | 5 | 5 |
| 90 | 20 | 0 | — | 5 | 5 |
| 91 | 20 | 0 | — | 5 | 4 |
| 92 | 20 | 0 | 5 | 5 | 5 |
|  | 10 | 0 | 4 | 5 | 5 |
| 93 | 20 | 0 | — | 5 | 5 |
| 94 | 20 | 0 | — | 5 | 5 |
| 95 | 20 | 0 | 4 | 5 | 5 |
| 96 | 20 | 0 | 4 | 5 | 5 |
| 97 | 20 | 0 | 4 | 5 | 5 |
|  | 10 | 0 | — | 5 | 5 |
| 98 | 20 | 0 | 5 | 5 | 5 |
|  | 10 | 0 | 4 | 5 | 5 |
| 99 | 20 | 0 | 4 | 5 | 5 |
|  | 10 | 0 | 4 | 5 | 5 |
| 100 | 20 | 0 | 4 | 5 | 5 |
| 101 | 20 | 0 | 4 | 5 | 5 |
|  | 10 | 0 | — | 5 | 5 |
| 102 | 20 | 0 | 4 | 5 | 5 |
| 103 | 20 | 0 | 5 | 5 | 5 |
|  | 10 | 0 | 4 | 5 | 5 |
| 104 | 20 | 0 | 4 | 5 | 5 |
| 105 | 20 | 0 | — | 5 | 5 |
| 106 | 20 | 0 | — | 5 | 4 |
| 107 | 20 | 0 | — | 5 | 4 |
| 108 | 20 | 0 | 4 | 5 | 5 |
| 109 | 20 | 0 | 4 | 5 | 5 |
| 110 | 20 | 0 | — | 5 | 4 |
| Control (a) | 40 | 0 | 0 | 2 | 1 |
|  | 20 | 0 | 0 | 1 | 0 |
| Control (b) | 40 | 1 | 0 | 3 | 2 |
|  | 20 | 0 | 0 | 2 | 0 |
| Control (c) | 40 | 1 | 1 | 3 | 3 |
|  | 20 | 1 | 0 | 1 | 2 |
| MCP | 20 | 3 | 4 | 5 | 5 |
|  | 10 | 3 | 3 | 5 | 5 |

EXAMPLE II (POST-EMERGENCE APPLICATION TEST (WEEDS))

Plastic trays (35 cm×25 cm×10 cm (high)) were filled with upland field soil, and the seeds of redroot pigweed, common lambsquarter, radish, sunflower, cocklebur, annual morningglory, black nightshade, large crabgrass, barnyard grass and green foxtail were separately sown in the trays and grown for 3 weeks in a green-house. The required amount of the test compound was sprayed to the foliage of the test plants over the top by means of a small hand sprayer. After the spraying, the test plants were grown for further 3 weeks in the green-house, and herbicidal activity was examined. The results are shown in Table 3. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, the weeds were in a 2- to 4-leaf stage and 2 to 12 cm in height although there was some difference depending upon the kind of weed.

TABLE 3

| Compound No. | Dosage (weight of active ingredient, g/are) | Redroot pigweed | Common lambs-quarter | Radish | Sunflower | Cock-lebur | Annual morning-glory | Black night-shade | Large crab-grass | Barnyard grass | Green foxtail |
| --- | --- | --- | --- | --- | --- | --- | --- | --- | --- | --- | --- |
| 3 | 20 | 5 | 5 | 5 | 5 | 5 | 5 | 5 | 4 | 4 | 4 |
| 4 | 20 | 5 | 5 | 5 | 5 | 5 | 4 | 5 | 4 | — | 4 |
| 6 | 20 | 3 | 5 | 5 | 5 | 4 | 5 | 5 | — | — | 4 |
| 7 | 20 | 5 | 5 | 5 | 5 | 5 | 5 | 5 | — | 4 | 4 |
| 8 | 20 | 5 | 5 | 5 | 5 | 5 | 5 | 5 | 5 | 4 | 4 |
|  | 10 | 5 | 5 | 5 | 5 | 5 | 5 | 5 | 4 | — | 4 |
| 10 | 20 | 5 | 5 | 5 | 5 | 4 | 5 | 5 | — | 4 | 4 |
| 12 | 20 | 5 | 5 | 5 | 5 | 5 | 5 | 5 | — | — | 4 |
| 14 | 20 | 5 | 5 | 5 | 5 | 5 | 5 | 5 | — | 5 | — |
| 15 | 20 | 5 | 5 | 5 | 5 | 5 | 5 | 5 | 4 | 5 | 4 |
| 16 | 20 | 5 | 5 | 5 | 5 | 5 | 5 | 5 | 4 | 5 | 5 |
|  | 10 | 5 | 5 | 5 | 5 | 5 | 5 | 5 | — | — | 4 |
| 17 | 20 | 5 | 5 | 5 | 5 | 5 | 5 | 5 | 5 | 4 | 5 |
| 18 | 20 | 5 | 5 | 5 | 5 | 5 | 5 | 5 | 4 | 5 | 5 |
|  | 10 | 5 | 5 | 5 | 5 | 5 | 5 | 5 | — | 4 | 5 |
| 19 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 5 |
| 20 | 20 | 5 | 5 | 5 | 5 | 5 | 5 | 5 | 5 | 5 | 5 |
|  | 10 | 5 | 5 | 5 | 5 | 5 | 5 | 5 | 5 | 4 | 4 |
| 21 | 20 | 5 | 5 | 5 | 5 | 5 | 5 | 5 | 4 | 5 | 5 |
|  | 10 | 5 | 5 | 5 | 5 | 5 | 5 | 5 | — | 5 | 4 |
| 22 | 20 | 5 | 5 | 5 | 5 | 5 | 5 | 5 | 5 | 4 | 5 |
| 23 | 20 | 5 | 5 | 5 | 5 | 5 | 4 | 5 | 4 | 4 | 4 |
| 26 | 20 | 5 | 5 | 5 | 5 | 5 | 5 | 5 | 4 | 5 | 5 |
|  | 10 | 5 | 5 | 5 | 5 | 5 | 5 | 5 | 4 | 4 | 4 |
| 27 | 20 | 5 | 5 | 5 | 5 | 5 | 5 | 5 | 4 | 5 | 5 |
|  | 10 | 5 | 5 | 5 | 4 | 5 | 4 | 5 | — | 4 | 4 |
| 29 | 20 | 5 | 5 | 5 | 5 | 5 | 5 | 5 | 4 | 4 | 4 |

TABLE 3-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambs-quarter | Radish | Sunflower | Cock-lebur | Annual morning-glory | Black night-shade | Large crab-grass | Barnyard grass | Green foxtail |
| 32 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 4 |
| 33 | 20 | 5 | 5 | 5 | 5 | 5 | 5 | 5 | 4 | 5 | 4 |
| | 10 | 5 | 5 | 5 | 5 | 5 | 5 | 5 | 4 | 4 | 4 |
| 35 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 5 |
| 36 | 20 | 5 | 5 | 5 | 5 | 5 | 5 | 5 | 5 | 4 | 5 |
| | 10 | 5 | 5 | 5 | 5 | 5 | 5 | 5 | 4 | 4 | 4 |
| 37 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 38 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 4 |
| 40 | 20 | 5 | 5 | 5 | 5 | 5 | 5 | 5 | 4 | 4 | 4 |
| 41 | 20 | 5 | 5 | 5 | 5 | 5 | 5 | 5 | 4 | 4 | 5 |
| 44 | 20 | 5 | 5 | 5 | 5 | 5 | 5 | 5 | 4 | 5 | 5 |
| | 10 | 5 | 5 | 5 | 5 | 5 | 5 | 5 | — | — | 4 |
| 45 | 20 | 5 | 5 | 5 | 5 | 5 | 5 | 5 | 4 | 4 | 5 |
| | 10 | 5 | 5 | 5 | 5 | 5 | 5 | 5 | 4 | 4 | 5 |
| 46 | 20 | 5 | 5 | 5 | 5 | 5 | 5 | 5 | 4 | — | 4 |
| 49 | 20 | 5 | 5 | 5 | 5 | 5 | 5 | 5 | 4 | 5 | 5 |
| 51 | 20 | 5 | 5 | 5 | 4 | 4 | 5 | 5 | 5 | 4 | 4 |
| 52 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 4 |
| 53 | 20 | 5 | 5 | 5 | 5 | 5 | 5 | 5 | 4 | 5 | 4 |
| 54 | 20 | 5 | 5 | 5 | 5 | 5 | 5 | 5 | 4 | 4 | 5 |
| 55 | 20 | 5 | 5 | 5 | 5 | 5 | 5 | 5 | 4 | 5 | 5 |
| 56 | 20 | 5 | 5 | 5 | 5 | 5 | 5 | 5 | 4 | 5 | 5 |
| | 10 | 5 | 5 | 5 | 5 | 5 | 5 | 5 | 4 | — | 5 |
| 57 | 20 | 5 | 5 | 5 | 5 | 5 | 5 | 5 | 5 | 4 | 5 |
| | 10 | 5 | 5 | 5 | 5 | 5 | 5 | 5 | 4 | 4 | 4 |
| 58 | 20 | 5 | 5 | 5 | 5 | 5 | 4 | 5 | 4 | — | 4 |
| 59 | 20 | 5 | 5 | 5 | 5 | 5 | 5 | 5 | 4 | 5 | 5 |
| | 10 | 5 | 5 | 5 | 5 | 5 | 5 | 5 | 4 | 4 | 5 |
| 60 | 20 | 5 | 5 | 5 | 5 | 5 | 5 | 5 | 5 | 4 | 5 |
| | 10 | 5 | 5 | 5 | 5 | 5 | 5 | 5 | 4 | — | 4 |
| 61 | 20 | 5 | 5 | 5 | 5 | 5 | 5 | 5 | — | 5 | 5 |
| 63 | 20 | 5 | 5 | 5 | 5 | 5 | 5 | 5 | 4 | 4 | 5 |
| 64 | 20 | 5 | 5 | 5 | 5 | 5 | 5 | 5 | 4 | 5 | 4 |
| 67 | 20 | 5 | 5 | 5 | 5 | 5 | 5 | 5 | 4 | 4 | 5 |
| 69 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 4 |
| 70 | 20 | 5 | 5 | 5 | 5 | 5 | 5 | 5 | — | 4 | 5 |
| 71 | 20 | 5 | 5 | 5 | 5 | 5 | 5 | 5 | 4 | 4 | 5 |
| 72 | 20 | 5 | 5 | 5 | 5 | 5 | 5 | 5 | 4 | 5 | 5 |
| 75 | 20 | 5 | 5 | 5 | 5 | 5 | 5 | 5 | — | 4 | — |
| 76 | 20 | 5 | 5 | 5 | 5 | 5 | 4 | 5 | — | 4 | 4 |
| 78 | 20 | 5 | 5 | 5 | 5 | 5 | 5 | 5 | — | — | 4 |
| 79 | 20 | 5 | 5 | 5 | 5 | 5 | 5 | 5 | 5 | 4 | 5 |
| | 10 | 5 | 5 | 5 | 5 | 5 | 5 | 5 | — | 4 | 4 |
| 80 | 20 | 5 | 5 | 5 | 5 | 5 | 5 | 5 | — | 4 | 4 |
| 81 | 20 | 5 | 5 | 5 | 5 | 5 | 5 | 5 | 4 | 4 | 4 |
| 83 | 20 | 5 | 5 | 5 | 5 | 5 | 5 | 5 | 4 | 4 | 4 |
| 84 | 20 | 5 | 5 | 5 | 5 | 5 | 5 | 5 | — | 4 | 5 |
| 85 | 20 | 5 | 5 | 5 | 5 | 5 | 5 | 5 | 4 | 5 | 5 |
| | 10 | 5 | 5 | 5 | 5 | 5 | 5 | 5 | 4 | — | 5 |
| 87 | 20 | 5 | 5 | 5 | 5 | 5 | 4 | 5 | — | 4 | 4 |
| 91 | 20 | 5 | 5 | 5 | 5 | 5 | 5 | 5 | 4 | — | 5 |
| 92 | 20 | 5 | 5 | 5 | 5 | 5 | 5 | 5 | 5 | 5 | 5 |
| | 10 | 5 | 5 | 5 | 5 | 5 | 5 | 5 | 4 | 3 | 3 |
| 94 | 20 | 5 | 5 | 5 | 5 | 5 | 5 | 5 | — | — | 4 |
| 95 | 20 | 5 | 5 | 5 | 5 | 5 | 5 | 5 | 4 | — | 4 |
| 96 | 20 | 5 | 5 | 5 | 5 | 5 | 5 | 5 | 4 | 4 | — |
| 97 | 20 | 5 | 5 | 5 | 5 | 5 | 5 | 5 | 4 | 5 | 5 |
| 98 | 20 | 5 | 5 | 5 | 5 | 5 | 5 | 5 | 5 | 5 | 5 |
| | 10 | 5 | 5 | 5 | 5 | 5 | 5 | 5 | 5 | 4 | 5 |
| 99 | 20 | 5 | 5 | 5 | 5 | 5 | 5 | 5 | 5 | 5 | 5 |
| | 10 | 5 | 5 | 5 | 5 | 5 | 5 | 5 | 4 | 4 | 5 |
| 100 | 20 | 5 | 5 | 5 | 5 | 5 | 5 | 5 | 4 | 5 | 5 |
| | 10 | 5 | 5 | 5 | 5 | 5 | 5 | 5 | — | — | 4 |
| 101 | 20 | 5 | 5 | 5 | 5 | 5 | 5 | 5 | 4 | 5 | 5 |
| | 10 | 5 | 5 | 5 | 5 | 5 | 5 | 5 | — | 4 | 4 |
| 102 | 20 | 5 | 5 | 5 | 5 | 5 | 5 | 5 | 5 | 5 | 4 |
| | 10 | 5 | 5 | 5 | 5 | 5 | 5 | 5 | — | 4 | — |
| 103 | 20 | 5 | 5 | 5 | 5 | 5 | 5 | 5 | 5 | 5 | 5 |
| | 10 | 5 | 5 | 5 | 5 | 5 | 5 | 5 | 4 | 5 | 5 |
| 104 | 20 | 5 | 5 | 5 | 5 | 5 | 5 | 5 | — | 4 | — |
| 105 | 20 | 5 | 5 | 5 | 5 | 5 | 5 | 5 | — | 4 | 4 |

TABLE 3-continued

| Compound No. | Dosage (weight of active ingredient, g/are) | Herbicidal activity | | | | | | | | | |
|---|---|---|---|---|---|---|---|---|---|---|---|
| | | Redroot pigweed | Common lambs-quarter | Radish | Sunflower | Cocklebur | Annual morning-glory | Black night-shade | Large crab-grass | Barnyard grass | Green foxtail |
| 108 | 20 | 5 | 5 | 5 | 5 | 5 | 5 | 5 | 5 | 5 | 5 |
| | 10 | 5 | 5 | 5 | 5 | 5 | 4 | 5 | 4 | — | 4 |
| 110 | 20 | 5 | 5 | 5 | 5 | 5 | 5 | 5 | 4 | 4 | 4 |
| Control (a) | 40 | 1 | 0 | 0 | 0 | 0 | 0 | 1 | 0 | 0 | 0 |
| | 20 | 0 | 0 | 0 | 0 | 0 | 0 | 0 | 0 | 0 | 0 |
| Control (b) | 40 | 0 | 0 | 1 | 0 | 0 | 0 | 0 | 0 | 0 | 0 |
| | 20 | 0 | 0 | 0 | 0 | 0 | 0 | 0 | 0 | 0 | 0 |
| Control (c) | 40 | 0 | 2 | 2 | 0 | 0 | 0 | 3 | 0 | 0 | 1 |
| | 20 | 0 | 0 | 0 | 0 | 0 | 0 | 1 | 0 | 0 | 0 |
| Bentazon | 20 | 3 | 5 | 5 | 5 | 5 | 4 | 5 | 1 | 2 | 0 |
| | 10 | 3 | 5 | 5 | 5 | 5 | 2 | 5 | 0 | 1 | 0 |
| Fluometuron | 20 | 5 | 5 | 5 | 5 | 5 | 5 | 5 | 5 | 5 | 5 |
| | 10 | 5 | 5 | 5 | 4 | 5 | 5 | 5 | 4 | 4 | 5 |
| Swep | 20 | 5 | 5 | 5 | 5 | 5 | 3 | 5 | 5 | 5 | 4 |
| | 10 | 5 | 4 | 4 | 5 | 5 | 3 | 3 | 2 | 4 | 4 |

EXAMPLE III (Post-emergence application test (cultivated plants))

Wagner's pots (1/5000 are) were each filled with upland field soil, and the seeds of soybean, cotton, sugar beet and wheat were sown in the pots and grown for 3 weeks in a green-house. The required amount of the test compound was sprayed to the foliage of the test plants over the top by means of a small hand sprayer. After the spraying, the test plants were grown for further 3 weeks in the greenhouse, and phytotoxicity was examined. In the above foliar application, the test compounds were each formulated into an emulsifiable concentrate, and the required amount of the emulsifiable concentrate was dispersed in water for application with the addition of wetting agent. At the time of application, soybean was in the second trifoliate stage, cotton in the 1-leaf stage, sugar beet in the 2-leaf stage and wheat in the 2-leaf stage. The results are shown in Table 4.

TABLE 4

| Compound No. | Dosage (weight of active ingredient, g/are) | Phytotoxicity | | | |
|---|---|---|---|---|---|
| | | Soybean | Cotton | Sugar beet | Wheat |
| 3 | 20 | 1 | — | — | 1 |
| 7 | 20 | 1 | — | — | — |
| 8 | 20 | — | — | — | 1 |
| | 10 | — | — | — | 0 |
| 36 | 20 | 1 | — | — | 0 |
| | 10 | 1 | — | — | 0 |
| 37 | 20 | — | — | 1 | 1 |
| | 10 | — | — | 1 | 0 |
| 38 | 20 | 1 | — | — | — |
| | 10 | 1 | — | — | — |
| 41 | 20 | 1 | — | — | 0 |
| 44 | 20 | 1 | — | — | 1 |
| | 10 | 1 | — | — | 0 |
| 45 | 20 | — | — | — | 1 |
| | 10 | — | — | — | 0 |
| 46 | 20 | 1 | — | 1 | 0 |
| 49 | 20 | 0 | 1 | — | — |
| 52 | 20 | 1 | 1 | — | — |
| | 10 | 0 | 0 | — | — |
| 56 | 20 | 0 | 0 | — | 1 |
| | 10 | 0 | 0 | — | 0 |
| 61 | 20 | 1 | — | — | 0 |
| | 10 | 1 | — | — | 0 |
| 60 | 20 | 1 | 1 | — | 1 |
| | 10 | 0 | 1 | — | 0 |
| 69 | 20 | 1 | — | — | — |
| | 10 | 1 | — | — | — |
| 71 | 20 | 0 | 1 | — | — |
| 76 | 20 | 1 | 0 | — | — |
| 79 | 20 | 0 | — | — | — |
| 81 | 20 | 1 | — | 0 | 0 |
| 84 | 20 | 1 | — | — | — |
| 85 | 20 | 0 | — | — | — |
| 98 | 20 | 1 | 0 | — | — |
| | 10 | 0 | 0 | — | — |
| 99 | 20 | — | — | 1 | 0 |
| | 10 | — | — | 0 | 0 |
| 101 | 20 | 1 | — | 1 | — |
| | 10 | 0 | — | 1 | — |
| 102 | 20 | 1 | — | 1 | — |
| | 10 | 0 | — | 0 | — |
| 103 | 20 | — | — | — | 1 |
| | 10 | — | — | — | 0 |
| Bentazon | 20 | 0 | — | 5 | — |
| | 10 | 0 | — | 5 | — |
| Fluometuron | 20 | — | 2 | — | — |
| | 10 | — | 1 | — | — |
| Swep | 20 | — | — | 5 | 3 |
| | 10 | — | — | 5 | 1 |

What is claimed is:

1. A compound of the formula:

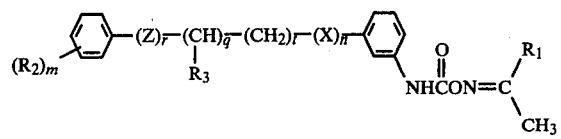

wherein $R_1$ is methyl or methoxy, $R_2$ is lower alkyl, lower alkoxy, methylenedioxy, methylthio, halogen or trifluoromethyl, $R_3$ is hydrogen, methyl or ethyl, X and Z are each oxygen or sulfur, m is an integer of 0 to 5 when $R_2$ is fluorine only or an integer of 0 to 3 when any $R_2$ is other than fluorine, $R_2$ being same or different in case of m being an integer of 2 or 3, n and r are each an integer of 0 or 1 but when one of them is zero, the other is not zero, q is an integer of 0 or 1 and t is an integer of 0 to 4 with the proviso that when $R_2$ is other than methylenedioxy, $R_1$ is not methyl.

2. The compound according to claim 1, wherein $R_1$ is methoxy, $R_2$ is lower alkyl, lower alkoxy or halogen, X is oxygen, m is an integer of 0 to 2, n is an integer of 1, r is an integer of 0, q is an integer of 1 and t is an integer of 1 to 4.

3. The compound according to claim 1, wherein $R_2$ is lower alkyl, lower alkoxy, halogen or trifluoromethyl, $R_3$ is hydrogen or methyl, Z is oxygen, m is an integer of 0 to 3, n is an integer of 0, r is an integer of 1, q is an integer of 1 and t is an integer of 0.

4. The compound according to claim 1, O-[N-{3-(3-trifluoromethylphenoxymethyl) phenyl}carbamoyl]methoxyethanaloxime.

5. The compound according to claim 1, O-[N-{3-(3,4-dichlorophenyl-3-propyloxy)phenyl}carbamoyl]methoxyethanaloxime.

6. The compound according to claim 1, O-[N-{3-(4-methylphenethyloxy)phenyl}carbamoyl]methoxyethanaloxime.

7. The compound according to claim 1, O-[N-{3-(3-chlorophenethyloxy)phenyl}carbamoyl]methoxyethanaloxime.

8. The compound according to claim 1, O-[N-{3-(4-tert-butylphenyloxymethyl)phenyl}carbamoyl]methoxyethanaloxime.

9. A herbicidal composition which comprises as an active ingredient a herbicidally effective amount of the compound according to claim 1 and a carrier therefor.

10. A method of selectively combating weeds in cultivation of soybean, cotton, sugar beet, rice or wheat, which comprises applying a herbicidally effective amount of the compound according to claim 1 to the area wherein the soybean, cotton, sugar beet, rice or wheat is cultivated.

* * * * *